United States Patent
Lo et al.

(10) Patent No.: US 10,893,830 B2
(45) Date of Patent: Jan. 19, 2021

(54) ELECTRONIC APPARATUS, SYSTEM, AND METHOD FOR PROVIDING BODY POSTURE HEALTH INFORMATION

(71) Applicant: Institute For Information Industry, Taipei (TW)

(72) Inventors: Yi-Ping Lo, Taipei (TW); Shih-Yao Wei, Taipei (TW)

(73) Assignee: Institute For Information Industry, Taipei (TW)

( * ) Notice: Subject to any disclaimer, the term of this patent is extended or adjusted under 35 U.S.C. 154(b) by 346 days.

(21) Appl. No.: 15/961,812

(22) Filed: Apr. 24, 2018

(65) Prior Publication Data

US 2019/0159719 A1    May 30, 2019

(30) Foreign Application Priority Data

Nov. 30, 2017 (TW) .............................. 106141882 A

(51) Int. Cl.
  *A61B 5/00* (2006.01)
  *A61B 5/0488* (2006.01)

(52) U.S. Cl.
  CPC .......... *A61B 5/4561* (2013.01); *A61B 5/0004* (2013.01); *A61B 5/0024* (2013.01);
  (Continued)

(58) Field of Classification Search
  CPC ... A61B 5/4519; A61B 5/6801; A61B 5/0004; A61B 5/0024; A61B 5/0488; A61B 2562/0219; A61B 5/4561
  See application file for complete search history.

(56) References Cited

U.S. PATENT DOCUMENTS

| | | |
|---|---|---|
| 2012/0215076 A1 | 8/2012 | Yang et al. |
| 2017/0027501 A1 | 2/2017 | Senanayake et al. |
| 2017/0156662 A1* | 6/2017 | Goodall ................. G16H 50/30 |

FOREIGN PATENT DOCUMENTS

| | | |
|---|---|---|
| CN | 105249943 A | 1/2016 |
| TW | 200939137 A | 9/2009 |

(Continued)

OTHER PUBLICATIONS

Office Action to the corresponding Taiwan Patent Application rendered by the Taiwan Intellectual Property Office (TIPO) dated Jun. 27, 2018, 16 pages (including English translation).

*Primary Examiner* — Christine H Matthews
*Assistant Examiner* — Joshua Daryl D Lannu
(74) *Attorney, Agent, or Firm* — Skaar Ulbrich Macari, P.A.

(57) ABSTRACT

An electronic apparatus, system, and method for providing body posture health information are provided. The method includes the steps of: calculating a posture data cluster based on signals detected by an inertial sensor disposed on a human body; comparing the posture data cluster with a plurality of preset posture data clusters individually to determine whether the posture data cluster matches one of the preset posture data clusters; if it matches one of the preset posture data clusters, generating a feedback message; calculating a plurality of muscle status indexes based on signals detected by electromyography sensors disposed on the human body; comparing the muscle status indexes with corresponding preset muscle status indexes individually to determine whether one of the muscle status indexes is abnormal; providing suggestion information in response to at least one of the muscle status indexes being abnormal; and displaying a multimedia corresponding to the suggestion information.

18 Claims, 5 Drawing Sheets

(52) U.S. Cl.
CPC .......... *A61B 5/0488* (2013.01); *A61B 5/4519* (2013.01); *A61B 5/6801* (2013.01); *A61B 2562/0219* (2013.01)

(56) References Cited

FOREIGN PATENT DOCUMENTS

| | | |
|---|---|---|
| TW | 201112179 A | 4/2011 |
| TW | 1347177 B | 8/2011 |
| TW | 201509487 A | 3/2015 |
| WO | 2015185420 A1 | 12/2015 |

\* cited by examiner

ELECTRONIC APPARATUS, SYSTEM, AND METHOD FOR PROVIDING BODY POSTURE HEALTH INFORMATION

PRIORITY

This application claims priority to Taiwan Patent Application No. 106141882 filed on Nov. 30, 2017, which is hereby incorporated by reference herein in its entirety.

FIELD

The present invention relates to an electronic apparatus, system, and method for providing health information, and more particularly, relates to an electronic apparatus, system, and method for providing corresponding health information according to body postures.

BACKGROUND

Because of the popularity of computer apparatuses and mobile devices, modern people often use smart phones with their head down or sit in front of desks to use computers for a long time every day. When people are busy with their work, it is hard for them to spare some time and get up off the desks to move around. Keeping the same posture for a long time or a poor posture tends to cause fatigue or stiffness of muscles at relevant parts of a human body, thereby influencing body health. For example, the fatigue or stiffness of muscles at the shoulder, the neck and the back of the human body is likely to cause annoying problems such as muscle soreness, migraine, dysautonomia, or scoliosis.

Accordingly, there is an urgent need in the art for an effective solution that is capable of providing body posture health information so as to prevent health problems of the human body such as muscle soreness, migraine, dysautonomia, or scoliosis caused by a poor posture or fatigue or stiffness of muscles.

SUMMARY

Embodiments of the present invention include an electronic apparatus, system, and method providing body posture health information.

The electronic apparatus comprises in one example embodiment a processor, a storage apparatus, and a display. The storage apparatus is electrically connected to the processor and is configured to store a computer program to be executed by the processor, a plurality of preset posture data clusters, and a plurality of preset muscle status indexes, wherein the computer program comprises a posture calculation program, a posture comparison program, a posture feedback program, a muscle status calculation program, a muscle status comparison program, and a muscle status feedback program. The posture calculation program is configured to calculate a posture data cluster based on an acceleration signal and an angular velocity signal that is detected by an inertial sensor disposed on at least one part of a human body. The posture comparison program is configured to compare the posture data cluster with each of the plurality of preset posture data clusters individually to determine whether the posture data cluster matches one of the preset posture data clusters. The posture feedback program is configured to generate a feedback message if the posture data cluster matches one of the preset posture data clusters. The muscle status calculation program is configured to calculate a muscle status index of each of a plurality of muscle groups on the human body based on a plurality of electromyography signals detected by a plurality of electromyography sensors disposed on the plurality of muscle groups of the human body. The muscle status comparison program is configured to compare the muscle status indexes with the corresponding preset muscle status indexes individually to determine whether each of the muscle status indexes is abnormal. The muscle status feedback program is configured to provide a piece of suggestion information in response to at least one of the muscle status indexes being abnormal, wherein the suggestion information corresponds to a multimedia. The display is configured to display the multimedia.

The system comprises in one example embodiment a processor, a communication apparatus, and a storage apparatus. The communication apparatus is electrically connected to the processor and communicates with an electronic apparatus via a remote network. The storage apparatus is electrically connected to the processor and is configured to store a computer program to be executed by the processor, a plurality of preset posture data clusters, and a plurality of preset muscle status indexes, wherein the computer program comprises a posture calculation program, a posture comparison program, a posture feedback program, a muscle status calculation program, a muscle status comparison program, and a muscle status feedback program. The posture calculation program is configured to calculate a posture data cluster based on an acceleration signal and an angular velocity signal that are detected by an inertial sensor disposed on at least one part of a human body. The posture comparison program is configured to compare the posture data cluster with each of the plurality of preset posture data clusters individually to determine whether the posture data cluster matches one of the preset posture data clusters. The posture feedback program is configured to generate a feedback message if the posture data cluster matches one of the preset posture data clusters. The muscle status calculation program is configured to calculate a muscle status index of each of a plurality of muscle groups on the human body based on a plurality of electromyography signals detected by a plurality of electromyography sensors disposed on the plurality of muscle groups of the human body. The muscle status comparison program is configured to compare the muscle status indexes with the corresponding preset muscle status indexes individually to determine whether each of the muscle status indexes is abnormal. The muscle status feedback program is configured to provide a piece of first suggestion information in response to at least one of the first muscle status indexes being abnormal. The communication apparatus transmits the first suggestion information to the electronic apparatus via the remote network so that a display of the electronic apparatus displays a multimedia corresponding to the first suggestion information.

The method in one example embodiment comprises the steps: calculating, by a processor, a posture data cluster based on an acceleration signal and an angular velocity signal that is detected by an inertial sensor disposed on at least one part of a human body; comparing, by the processor, the posture data cluster with each of a plurality of preset posture data clusters individually to determine whether the posture data cluster matches one of the preset posture data clusters; generating, by the processor, a feedback message if the posture data cluster matches one of the preset posture data clusters; calculating, by the processor, a muscle status index of each of a plurality of muscle groups on the human body based on a plurality of electromyography signals detected by a plurality of electromyography sensors disposed on the plurality of muscle groups of the human body; comparing, by the processor, the muscle status indexes with the corresponding preset muscle status indexes individually to determine whether each of the muscle status indexes is abnormal; providing, by the processor, a piece of suggestion information in response to at least one of the muscle status indexes being abnormal; and displaying, by a display, a multimedia corresponding to the suggestion information.

According to the above descriptions, when the processor determines a poor body posture or an abnormal muscle status according to the signals detected by the inertial sensor and the electromyography sensors, a feedback signal for posture adjustment or suggestion information for improving the abnormal muscle status can be provided in real time. A corresponding multimedia can be displayed by the display to guide the user to adjust the posture or take exercises for improving the muscle status. Through the electronic apparatus, system, and method for providing body posture health information provided in the present invention, health problems of the human body such as muscle soreness, migraine, dysautonomia, or scoliosis caused by a poor posture or fatigue or stiffness of muscles can be solved.

This summary overall describes the present invention (covers the problem to be solved, the means to solve the problem, and the effect of the present invention) to provide a basic understanding of the present invention. This summary is not intended to encompass all embodiments of the present invention. Additionally, this summary is neither intended to confirm essential or necessary elements of any or all embodiments of the present invention, nor intended to describe the scope of any or all embodiments of the present invention. This summary is provided only to present some concepts of part embodiments of the present invention in a simple form and as an introduction to the following detailed description.

DETAILED DESCRIPTION

Example embodiments of the present invention described below are not intended to limit the present invention to any environment, applications, structures, processes, or steps described in these example embodiments. In the attached drawings, elements unrelated to the present invention are omitted from depiction; and dimensions of and dimensional scales among individual elements in the attached drawings are only examples but not intended to limit the present invention. Unless stated particularly, same (or similar) element symbols may correspond to same (or similar) elements in the following description.

Figure 1:
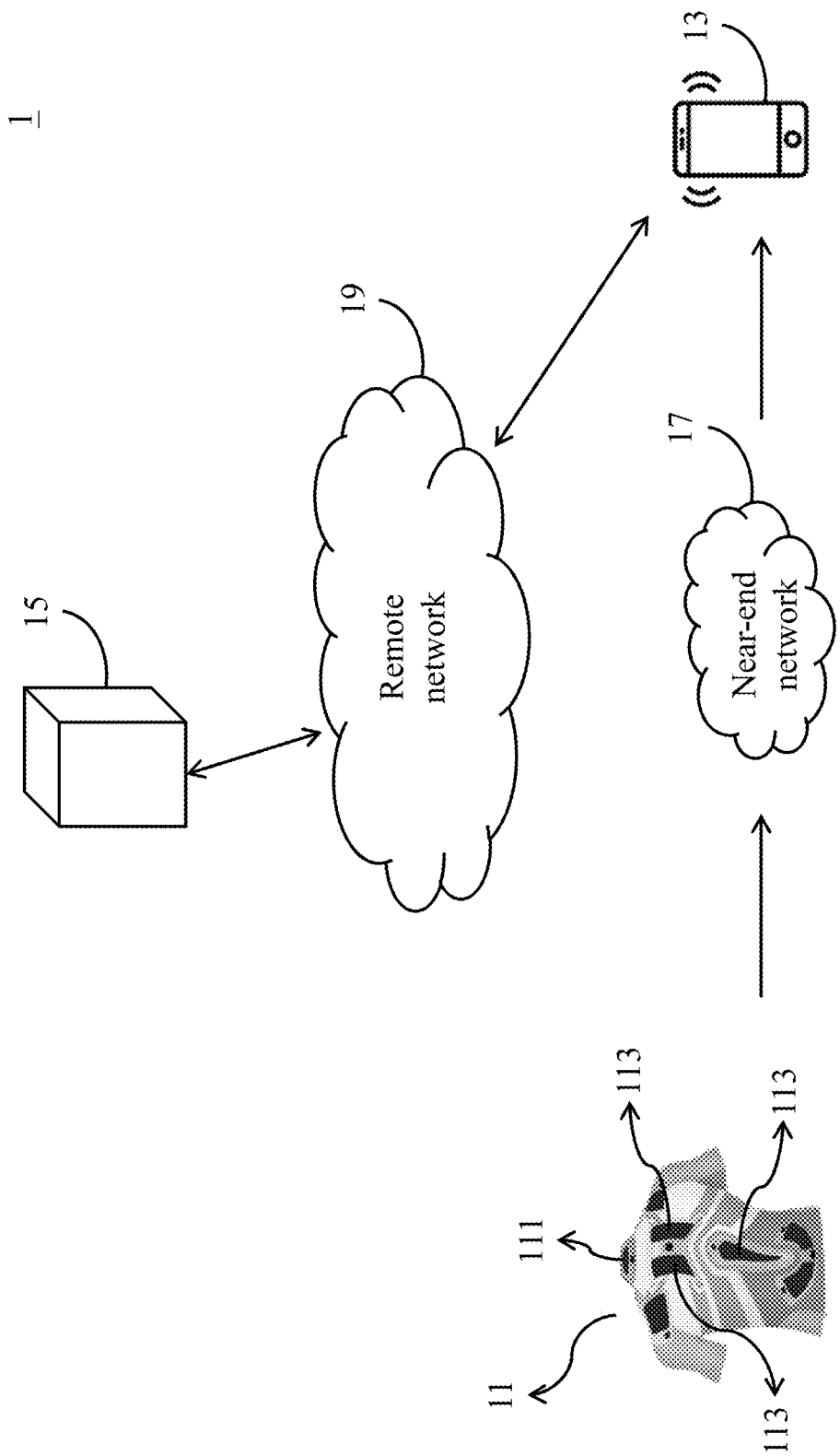
FIG. 1 is a schematic view illustrating a communication network environment for providing body posture health information in one or more embodiments of the present invention.

FIG. 1 is a schematic view illustrating a communication network environment 1 for providing body posture health information in one or more embodiments of the present invention. The communication network environment 1 for providing body posture health information shown in FIG. 1 comprises a wearable apparatus 11, an electronic apparatus 13, and a cloud service system 15. The wearable apparatus 11 communicates with the electronic apparatus 13 via a near-end network 17, and the electronic apparatus 13 communicates with the cloud service system 15 via a remote network 19.

The wearable apparatus 11 may be one of various sensing apparatuses that can be worn by a human body such as smart clothes, a smart vest, a smart chest belt, a smart waistband, a patch sensor, or the like but not limited thereto. The wearable apparatus 11 comprises at least one inertial sensor 111 and a plurality of electromyography sensors 113, and the inertial sensor 111 and the electromyography sensors 113 are all electrically connected to the wearable apparatus 11. The wearable apparatus 11 transmits signals detected by the inertial sensor 111 and the electromyography sensors 113 to the electronic apparatus 13 via the near-end network 17. The inertial sensor 111 may comprise a tri-axial accelerometer, a tri-axial gyroscope, and a tri-axial magnetometer. When a user wears the wearable apparatus 11, the inertial sensor 111 is disposed on at least a part (e.g., the neck, the shoulder, the back, the waist, but not limited thereto) of a human body to detect acceleration signals and angular velocity signals of the human body in the three-dimensional space. Moreover, when the user wears the wearable apparatus 11, the electromyography sensors 113 are disposed on a plurality of muscle groups (e.g. trapezius, rhomboideus, or serratus anterior but not limited thereto) on the human body respectively to detect a plurality of electromyography signals corresponding to the muscle groups. The electromyography sensors 113 may be attached on the surface of the skin on the muscle groups being detected. For example, each of the electromyography sensors 113 may be a surface electromyography (SEMG) sensor, but it is not limited thereto.

The electronic apparatus 13 may be one of various types of electronic apparatus such as a smart phone, a notebook computer, a tablet computer, a desktop computer, a smart watch, or the like, but not limited thereto. The electronic apparatus 13 may receive the acceleration signals and angular velocity signals detected by the inertial sensor 111 via the near-end network 17 to calculate a real-time posture data cluster of the human body and compare the real-time posture data cluster with a plurality of preset posture data clusters, thereby determining whether the real-time posture of the human body is correct or not. If the real-time posture is incorrect, the electronic apparatus 13 immediately provides an incorrect posture prompting message to notify the user that he/she is in an incorrect posture so that the user can adjust the posture thereof. Additionally, the electronic apparatus 13 may receive electromyography signals detected by each of the electromyography sensors 113 via the near-end network 17 to calculate real-time muscle status indexes of the muscle groups on the human body and compare each of the real-time muscle status indexes with corresponding preset muscle status indexes individually, thereby determining whether each of the real-time muscle status indexes is normal or abnormal. If one of the real-time muscle status indexes is abnormal, the electronic apparatus 13 immediately provides a piece of suggestion information for reference of the user to improve the muscle status. The aforesaid suggestion information may be but not limited to suggestion information of doing neck and shoulder stretching exercises so that the user can make reference to the suggestion information to achieve the effect of relaxing muscles.

In some embodiments, the electronic apparatus 13 receives and temporarily stores the signals detected by inertial sensor 111 and the electromyography sensors 113 and transmits the aforesaid signals to the cloud service system 15 via the remote network 19, and then the cloud service system 15 executes the aforesaid calculating, comparing, and determining operations executed by the electronic apparatus 13. In some embodiments, the electronic apparatus 13 receives and temporarily stores the signals detected by inertial sensor 111 and the electromyography sensors 113 and preliminarily processes the signals detected by inertial sensor 111 and the electromyography sensors 113 (e.g., calculates the real-time posture data cluster of the human body, calculates the real-time muscle status indexes of the muscle groups of the human body as described above), and then the cloud service system 15 executes the aforesaid comparing and determining functions executed by the electronic apparatus 13. In other words, in some embodiments, the aforesaid calculating capability of the electronic apparatus 13 may be supported by the cloud service system 15 so as to handle demands of big data processing.

The cloud service system 15 is a computer system having a cloud calculation capability, such as various service systems built in the cloud network but not limited thereto. The cloud service system 15 communicates with the aforesaid electronic apparatus 13 via the remote network 19. As described previously, in some embodiments, the cloud service system 15 may execute the calculating, comparing, and determining functions that are originally executed by the electronic apparatus 13 so as to support the electronic apparatus 13 in big data processing, and other details thereof will not be further described herein.

The near-end network 17 may be a wireless sensor network (which is called WSN for short), such as a Bluetooth, a Bluetooth low energy (BLE), a Wi-Fi, a Zigbee, a Near Field Communication (NFC), an infrared ray, or other short-distance wireless communication technologies but not limited thereto.

The remote network 19 may be a wired network, a mobile communication network, or a wireless network, such as a 3G, 4G, or 5G mobile communication system, a wide area network (WAN), or a local area network (LAN) but not limited thereto.

Figure 2:
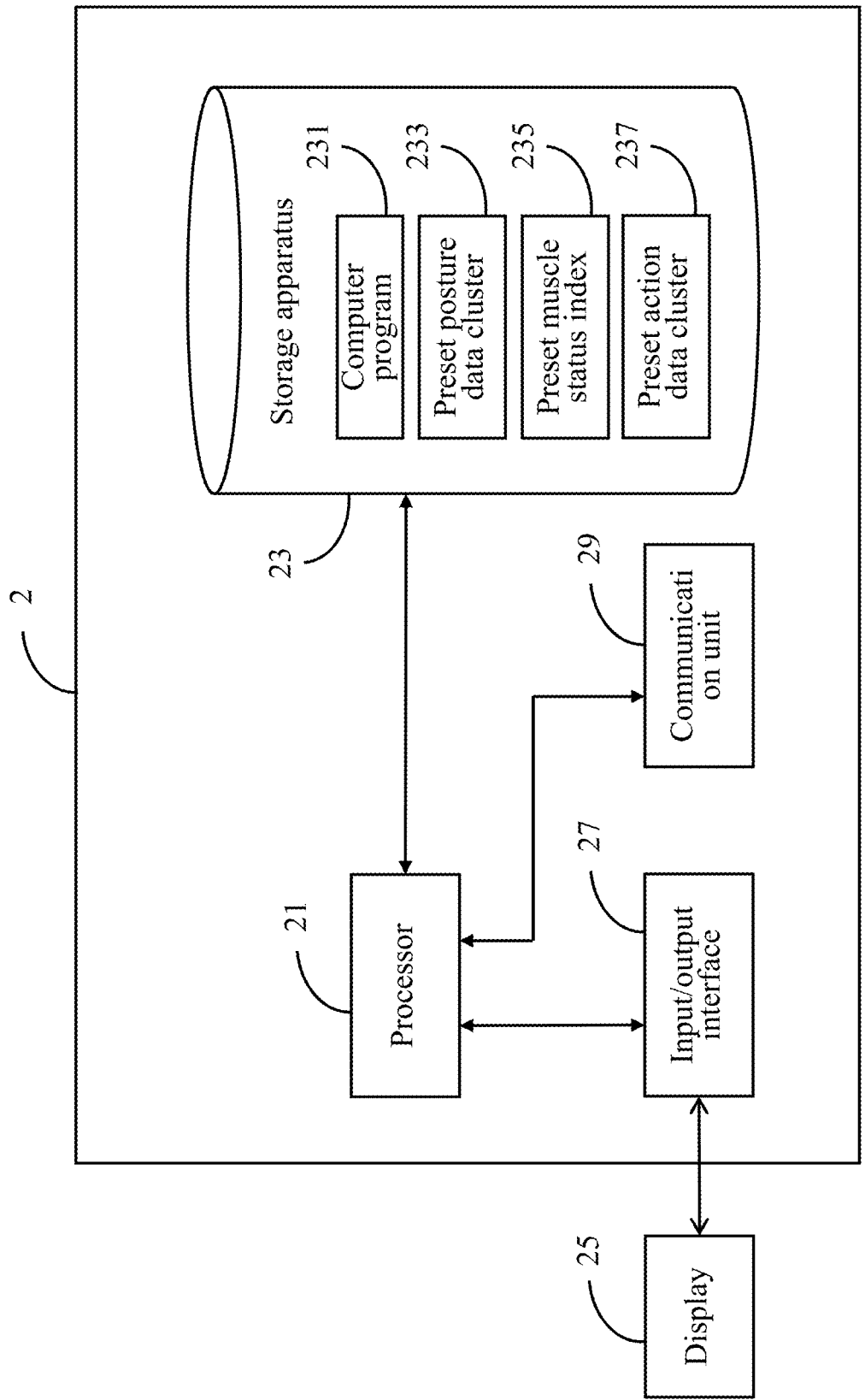
FIG. 2 is a block diagram illustrating an electronic apparatus for providing body posture health information in one or more embodiments of the present invention.

FIG. 2 is a block diagram illustrating an electronic apparatus 2 for providing body posture health information in one or more embodiments of the present invention. The electronic apparatus 2 comprises a processor 21 and a storage apparatus 23. The electronic apparatus 2 may further comprise other elements such as a display 25, an input/output interface 27, and a communication unit 29 but not limited thereto. The electronic apparatus 2 may electrically connect, via some mediums or elements (e.g., various buses), the processor 21, the storage apparatus 23, the input/output interface 27, and the communication unit 29 (i.e., indirect electrical connection). Alternatively, the electronic apparatus 2 may electrically connect, not via some mediums or elements, the processor 21, the storage apparatus 23, the input/output interface 27, and the communication unit 29 (i.e., direct electrical connection). The electronic apparatus 2 may transmit signals and change data among the processor 21, the storage apparatus 23, the input/output interface 27, and the communication unit 29 through the direct electrical connection or the indirect electrical connection. The electronic apparatus 2 may be one of various types of calculating apparatuses, such as a smart phone, a notebook computer, a tablet computer, a desktop computer, a smart watch, or the like but not limited thereto. In some embodiments, the aforesaid processor 21, the storage apparatus 23 and the input/output interface 27 may be comprised in a same chip, e.g., a micro control unit (MCU).

The processor 21 may be a central processing unit (CPU) of a general calculating apparatus/computer, and may be programmed to interpret computer instructions, process data in computer software and execute various operational programs. The central processing unit may be a processor constituted by a plurality of independent units or a microprocessor constituted by one or more integrated circuits.

The storage apparatus 23 may comprise various storage units comprised in a general calculating apparatus/computer. The storage apparatus 23 may comprise a primary memory which is also called a main memory or an internal memory, and the primary memory communicates direct to the central processing unit. The central processing unit may read instruction sets stored in the primary memory, and execute these instruction sets if needed. The storage apparatus 23 may further comprise a secondary memory which is also called an external memory or an auxiliary memory, and the secondary memory connects to the central processing unit through an I/O channel of the secondary memory instead of directly connecting to the central processing unit, and uses a data buffer to transmit data to the primary memory. The data in the secondary memory does not disappear even in the case without power supply (i.e., is non-volatile). The secondary memory may for example be various types of hard disks, optical disks or the like. The storage apparatus 23 may also comprise a third-level storage apparatus, i.e., a storage apparatus that can be inserted into or pulled out from a computer directly, e.g., a mobile disk.

The display 25 has the function of providing display data to the user, and may be one of various types of screens but not limited thereto.

The input/output interface 27 may provide the connection between the electronic apparatus 2 and external apparatuses and allows data of various external apparatuses to be inputted into or outputted from the electronic apparatus 2. The external apparatus may be a keyboard, a touch screen, or other suitable input apparatuses but not limited thereto. The external apparatus may also include a portable computer readable recording medium, e.g., a mobile disk, a portable optical disk and a memory card. In some embodiments, the computer program and data may be stored on a portable computer readable recording medium and may be loaded on the storage apparatus 23 via the input/output interface 27. The input/output interface 27 may also connect to the display 25.

The communication unit 29 may be at least one physical network interface card comprised in a general computer to serve as an interconnection point between the electronic apparatus 2 and a network, and the network may be a private network (e.g., a local area network) or a public network (e.g., the Internet). Depending on different requirements, the communication unit 29 may enable the electronic apparatus 2 to communicate and exchange data with other electronic apparatuses on the network by wired access or wireless access. In some embodiments, apparatuses such as a switching apparatus, a route apparatus or the like may also be included between the communication unit 29 and the network.

The electronic apparatus 2 may be configured to provide body posture health information. Examples are described hereinafter for purpose of illustration only, which are not intended to limit the present invention. The storage apparatus 23 stores a computer program 231 to be executed by the processor 21, a plurality of preset posture data clusters 233, and a plurality of preset muscle status indexes 235. The aforesaid computer program 231 comprises a posture calculation program, a posture comparison program, a posture feedback program, a muscle status calculation program, a muscle status comparison program, and a muscle status feedback program.

In some embodiments, the preset posture data clusters 233 may comprise a plurality of correct posture data clusters and a plurality of incorrect posture data clusters. In some embodiments, inertial sensing signals may be detected by one or more inertial sensors in advance for one or more testees or persons at some posture(s), and then these inertial sensing signals are used to establish the preset posture data cluster 233 through a machine learning algorithm. The aforesaid machine learning algorithm may be a supervised learning algorithm, e.g., a convolutional neural network (CNN). The aforesaid machine learning algorithm may also be an unsupervised learning algorithm. Applicable algorithms may be selected depending on actual requirements to achieve the aforesaid machine learning in the embodiments.

In some embodiments, the preset muscle status indexes 235 may comprise a corresponding root mean square (RMS) of a plurality of electromyography signals and/or a corresponding median frequency (MDF) of a plurality of electromyography signals. The preset muscle status indexes 235 may be acquired in advance, e.g., electromyography signals of muscle groups of one or more testees or persons are collected in advance by the electromyography sensors, and then time frequency analysis is performed on each of the electromyography signals to generate a time-domain electromyography signal and a frequency-domain electromyography signal. It shall be appreciated that the time-domain electromyography signal is mainly used to calculate the RMS of the electromyography signals, and the RMS is an index for representing the amplitude of the electromyography signals and is used to evaluate the intensity of the load on the muscles. The larger the load on the muscles is, the larger the RMS of the electromyography signals will be. The frequency-domain electromyography signal is mainly used to calculate the MDF of the electromyography signals, and the MDF is an index for representing the degree of fatigue of the muscles. The degree of fatigue of the muscles may be evaluated according to the movement of the MDF to the low frequency. Specifically, the MDF will be remarkably reduced as the degree of fatigue of the muscles increases (i.e., moves to the low frequency).

In some embodiments, when the user wears the wearable apparatus 11 which is provided with the inertial sensor 111 and a plurality of electromyography sensors 113, it means that the inertial sensor 111 is provided on at least one part (e.g. the neck, the shoulder, the back, and the waist but not limited thereto) of a human body and detects a first acceleration signal and a first angular velocity signal. The first acceleration signal and the first angular velocity signal being detected correspond to the at least one part where the inertial sensor 111 is provided. The inertial sensor 111 transmits the detected first acceleration signal and the first angular velocity signal to the communication unit 29 via the near-end network. After the communication unit 29 receives the first acceleration signal and the first angular velocity signal from the inertial sensor 111, the processor 21 executes the posture calculation program of the computer program 231, i.e., the processor 21 calculates a real-time posture data cluster according to the first acceleration signal and the first angular velocity signal detected by the inertial sensor 111.

Moreover, the processor 21 further executes a posture comparison program and a posture feedback program of the computer program 231. The posture comparison program executed by the processor 21 compares the real-time posture data cluster with each of the preset posture data clusters 233 individually to determine whether the real-time posture data cluster matches one of the preset posture data clusters 233. When the real-time posture data cluster matches one of the preset posture data clusters 233, a feedback message is generated. Specifically, when the real-time posture data cluster matches a correct posture data cluster among the preset posture data clusters 233, the feedback message is a correct posture prompting message (i.e., notifying the user that the posture thereof is correct). When the real-time posture data cluster matches an incorrect posture data cluster among the preset posture data clusters 233, the feedback message is an incorrect posture prompting message (i.e., prompting the user that the posture thereof is incorrect and should be adjusted). In some embodiments, when the real-time posture data cluster does not match any of the preset posture data clusters 233, a feedback message may also be generated (i.e., notifying the user that the posture thereof belongs to other postures).

In some embodiments, the feedback message may be a tactile, auditory, or visual feedback message. For ease of understanding, an example where the feedback message is a tactile feedback message will be described hereby, which, however, is not intended to limit the scope of the present invention. The feedback message may be a vibration feedback message of the tactile feedback message, the electronic apparatus 2 may transmit the vibration feedback message to the wearable apparatus 11 via the communication unit 29, and a vibrator on the wearable apparatus 11 vibrates in response to the vibration feedback message so as to prompt the user. Alternatively, if the electronic apparatus 2 is provided with a vibrator, the vibrator may also vibrate in response to the vibration feedback message to achieve the same prompting effect. Similarly, if the feedback message is an auditory feedback message or a visual feedback message, the electronic apparatus 2 may also transmit the auditory feedback message or the visual feedback message to a corresponding apparatus (e.g., a loudspeaker, an earphone or a screen) so that the apparatus issues an alert message in response to the feedback message to achieve the effect of prompting the user. The specific implementation thereof shall be appreciated by those of ordinary skill in the art based on the above descriptions, and thus will not be further described herein.

In some embodiments, the plurality of electromyography sensors 113 are disposed on a plurality of muscle groups (e.g. trapezius, rhomboideus, and serratus anterior but not limited thereto) on the human body respectively to detect a first electromyography signal of each of the muscle groups. Each of the electromyography sensors 113 transmits the detected first electromyography signal to the communication unit 29 via the near-end network. After the communication unit 29 receives the first electromyography signals detected by the electromyography sensors 113, the processor 21 executes the muscle status calculation program of the computer program 231, i.e., the processor 21 calculates a first muscle status index of each of the muscle groups according to each of the first electromyography signals. For example, each of the electromyography sensors 113 may be a sensor attached on the surface of the skin on the muscle group being detected, such as a surface electromyography (SEMG) sensor but not limited thereto. Each of the aforesaid first muscle status indexes may comprise a corresponding RMS of the first electromyography signals and/or a corresponding MDF of the first electromyography signals.

Moreover, the processor 21 further executes the muscle status comparison program and the muscle status feedback program of the computer program 231. The muscle status comparison program executed by the processor 21 compares the first muscle status indexes with the corresponding preset muscle status indexes 235 individually to determine whether each of the first muscle status indexes is abnormal. The muscle status feedback program executed by the processor 21 provides a piece of first suggestion information in response to at least one of the first muscle status indexes being abnormal.

In some embodiments, the first suggestion information may be tactile, auditory, or visual suggestion information. For ease of understanding, an example where the first suggestion information is a piece of tactile suggestion information will be described hereby, which, however, it is not intended to limit the scope of the present invention. The first suggestion information may be vibration suggestion information of the tactile suggestion information, the electronic apparatus 2 may transmit the tactile suggestion information to the wearable apparatus 11 via the communication unit 29, and a vibrator on the wearable apparatus 11 vibrates in response to the tactile suggestion information so as to prompt the user. Alternatively, if the electronic apparatus 2 is provided with a vibrator, the vibrator may also vibrate in response to the tactile suggestion information to achieve the same prompting effect. Similarly, if the first suggestion information is a piece of auditory suggestion information or visual suggestion information, the electronic apparatus 2 may also transmit the auditory suggestion information or the visual suggestion information to a corresponding apparatus (e.g., a loudspeaker, an earphone, or a screen) so that the apparatus issues an alert message in response to the suggestion information to achieve the effect of prompting the user.

For example, if the muscle status index of the trapezius is abnormal among the first muscle status indexes, the electronic apparatus 2 may instruct the display 25 to provide the first suggestion information in the form of an image or animation (e.g., prompt and suggest the user to do lateral stretching exercises for the neck or rotational and stretching exercises for the shoulder to stretch the trapezius so as to improve the fatigue or stiffness of the muscles on the shoulder and the neck). In some embodiments, the display 25 may be a touch screen used for displaying the first suggestion information, and the first suggestion information may comprise corresponding menus of various different stretching exercises (which are for example but not limited to pull-down menus or pop-up menus) to be selected by the users.

In some embodiments, the first suggestion information may correspond to a multimedia, and the multimedia may be displayed on the display 25. When the user selects one or more stretching exercises via the pull-down menus or the pop-up menus, the display 25 displays the corresponding multimedia. The multimedia may be a film about stretching exercises so as to guide the user to stretch corresponding muscle groups which are abnormal. The multimedia may also be an interactive multimedia such as an interactive motion sensing game but not limited there to, and the interactive motion sensing game may comprise various games corresponding to various stretching exercises respectively. For example, the aforesaid interactive motion sensing game may be designed to be a fighter game which corresponds to a shoulder stretching exercise. In this fighter game, the user may control the movement of the fighter to the left and the right to avoid enemy fighters or obstacles by shaking the head thereof to the left and the right, thereby stretching the trapezius on the left and the right shoulders. Therefore, when the first suggestion information corresponds to the interactive motion sensing game, the purpose of improving the fatigue or stiffness of the muscles can be achieved, and meanwhile interestingness of the stretching exercises can be increased and the degree of participation of the user in the stretching exercises can be improved.

In some embodiments, the storage apparatus 23 further stores a plurality of preset action data clusters 237, and each of the preset action data clusters 237 comprises a plurality of sub-action data clusters that are sequential within a time period. Specifically, inertial sensing signals may be sensed in advance by one or more inertial sensors from one or more testees or persons when they finish one or more action trajectories within a certain period of time, and one or more preset action data clusters are established from these inertial sensing signals via a machine learning method. Each of the aforesaid action trajectories refers to changes in posture of a testee or a person within a certain period of time and is formed of a plurality of successive postures. Therefore, each of the sub-action clusters refers to a posture data cluster at a certain time point of each preset action data cluster 237. Taking the stretching sport as an example, each of the preset action data clusters 237 is calculated based on inertial sensing signals received when each of the testees or persons does the corresponding stretching sport.

In some embodiments, the preset action data clusters 237 may comprise a plurality of standard action data clusters, and the multimedia corresponding to the first suggestion information corresponds to at least one of the preset action data clusters 237. In these embodiments, the computer program 231 further comprises an action calculation program, an action comparison program, and an action feedback program.

In some embodiments, when the user does the corresponding stretching sport according to the multimedia displayed on the display 25, the inertial sensor 111 detects a second acceleration signal and a second angular velocity signal, and transmits the detected second acceleration signal and the second angular velocity signal to the communication unit 29 via the near-end network. After the communication unit 29 receives the second acceleration signal and the second angular velocity signal from the inertial sensor 111, the processor 21 executes the action calculation program of the computer program 231. That is, the processor 21 calculates a real-time action data cluster according to the second acceleration signal and the second angular velocity signal detected by the inertial sensor 111.

Moreover, the processor 21 further executes the action comparison program and the action feedback program of the computer program 231. The action comparison program executed by the processor 21 compares the real-time action data cluster with the at least one preset action data cluster corresponding to the multimedia to decide an action similarity. The aforesaid action similarity is decided by the processor 21 according to a Dynamic Time Warping (DTW) algorithm and/or a Euclidean distance. When the action similarity is lower than a threshold, it means that the real-time action data cluster is not a standard action data cluster, i.e., the action of the user is wrong or incorrect. The action feedback program executed by the processor 21 provides a piece of second suggestion information when the action similarity is lower than a threshold, thereby prompting the user to adjust the wrong or incorrect action. The implementation of the second suggestion information is similar to that of the aforesaid first suggestion information, and thus will not be further described herein.

In some embodiments, when the user does the corresponding stretching sport according to the multimedia displayed on the display 25, each of the electromyography sensors 113 detects a second electromyography signal and transmits the detected second electromyography signal to the communication unit 29 via the near-end network. After the communication unit 29 receives the second electromyography signals detected by the electromyography sensors 113, the processor 21 executes the muscle status calculation program of the computer program 231. That is, the processor 21 calculates a second muscle status index of each of the plurality of muscle groups according to each of the second electromyography signals. Each of the aforesaid second muscle status indexes may comprise a corresponding root mean square (RMS) of the second electromyography signals and/or a corresponding median frequency (MDF) of the second electromyography signals. Moreover, the muscle status comparison program executed by the processor 21 compares the second muscle status indexes with the corresponding preset muscle status indexes individually to determine whether each of the second muscle status indexes is abnormal. The muscle status feedback program executed by the processor 21 provides a piece of advanced suggestion information when at least one of the second muscle status indexes is abnormal. The advanced suggestion information may be used to prompt that the muscle status of the user has not yet been improved, and the corresponding stretching sport needs to be done again. Alternatively, the advanced suggestion information represents that the muscle status of the user has been improved, and an advanced stretching sport is suggested to strengthen the muscle status. In some embodiments, the implementation of the advanced suggestion information is similar to that of the aforesaid first suggestion information, and thus will not be further described herein.

Figure 3:
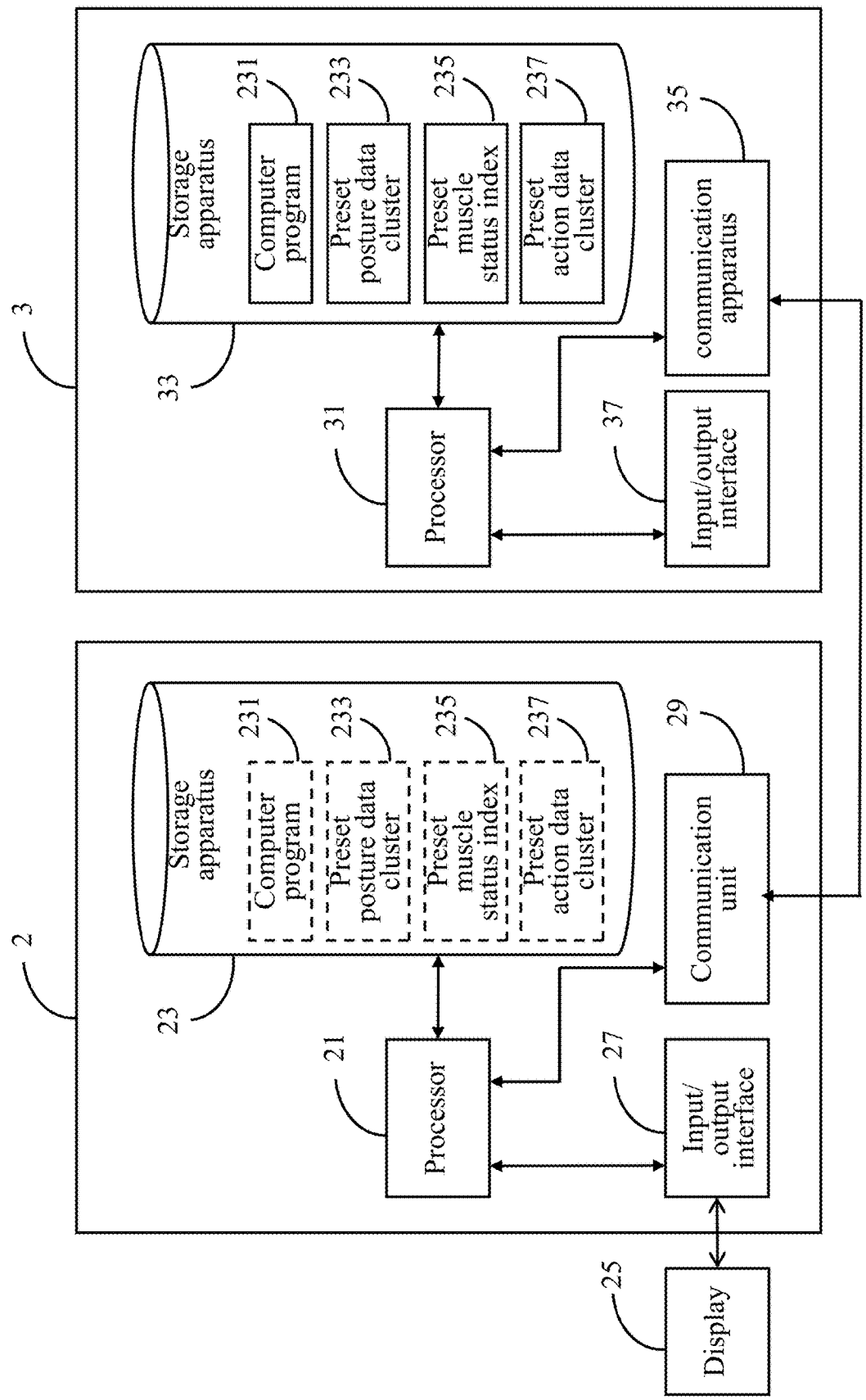
FIG. 3 is a block diagram illustrating communication between a cloud service system for providing body posture health information and an electronic apparatus via a network in one or more embodiments of the present invention.

FIG. 3 is a block diagram of a system for providing body posture health information according to one or more embodiments of the present invention. The system is a cloud service system 3, and it communicates with an electronic apparatus 2 via a network. The cloud service system 3 comprises a processor 31, a storage apparatus 33, and a communication apparatus 35. The cloud service system 3 may further comprise other elements, such as an input/output interface 37 but not limited thereto. The cloud service system 3 may electrically connect, via some mediums or elements (e.g., various buses), the processor 31, the storage apparatus 33, the communication service 35, and the input/output interface 37 (i.e., indirect electrical connection). Alternatively, the cloud service system 3 may electrically connect, not via some mediums or elements, the processor 31, the storage apparatus 33, the communication apparatus 35 and the input/output interface 37 (i.e., direct electrical connection). The cloud service system 3 may transmit signals and change data among the processor 31, the storage apparatus 33, the communication apparatus 35 and the input/output interface 37 through the direct electrical connection or the indirect electrical connection.

In some embodiments, the cloud service system 3 is a computer system capable of cloud calculation, such as other similar service systems built in the cloud network but not limited thereto. The cloud service system 3 communicates with the aforesaid electronic apparatus 2 via the remote network. In some embodiments, the storage apparatus 33 of the cloud service system 3 may store a computer program 231, the preset posture data clusters 233, the preset muscle status indexes 235, and the preset action data clusters 237 for executing the aforesaid calculating, comparing and determining functions executed by the electronic apparatus 2, thereby supporting the electronic apparatus 2 in big data processing. In these embodiments, the storage apparatus 23 of the electronic apparatus 2 may not store the computer program 231, the preset posture data clusters 233, the preset muscle status indexes 235 and the preset action data clusters 237. In these embodiments, the processes of the calculating, comparing and determining operations executed by the cloud service system 3 are the same as these executed by the aforesaid electronic apparatus 2, and thus will not be further described herein. The feedback message, the first suggestion information, the second suggestion information, and the advanced suggestion information generated by the cloud service system 3 are transmitted to the electronic apparatus 2 via the remote network and displayed on the display 25. Implementations of the aforesaid feedback message, the first suggestion information, the second suggestion information, and the advanced suggestion information have also been disclosed in one or more embodiments of the aforesaid electronic apparatus 2, and thus will not be further described herein.

Figure 4A:
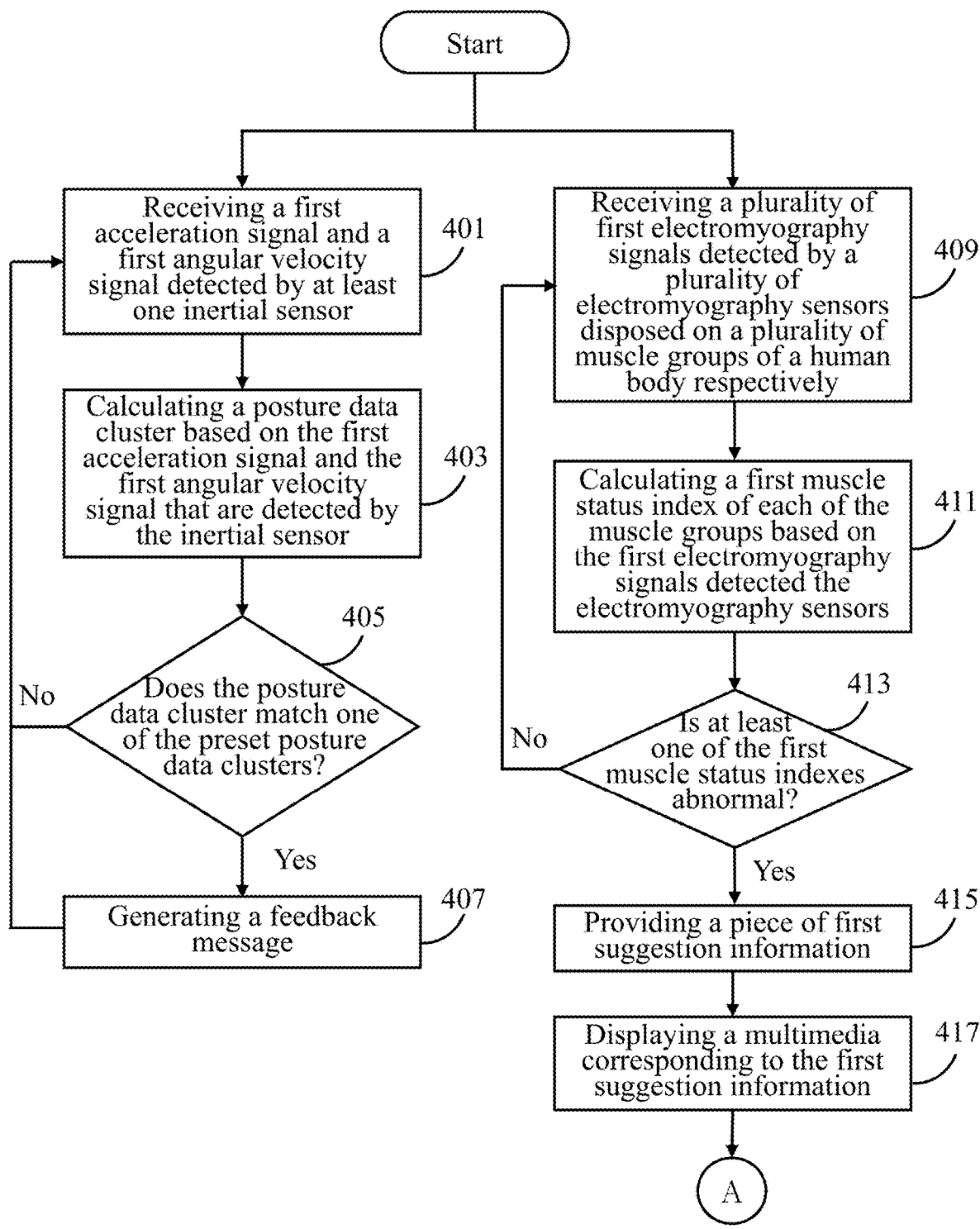
FIG. 4A is a flowchart illustrating a method for providing body posture health information in one or more embodiments of the present invention.
Figure 4B:
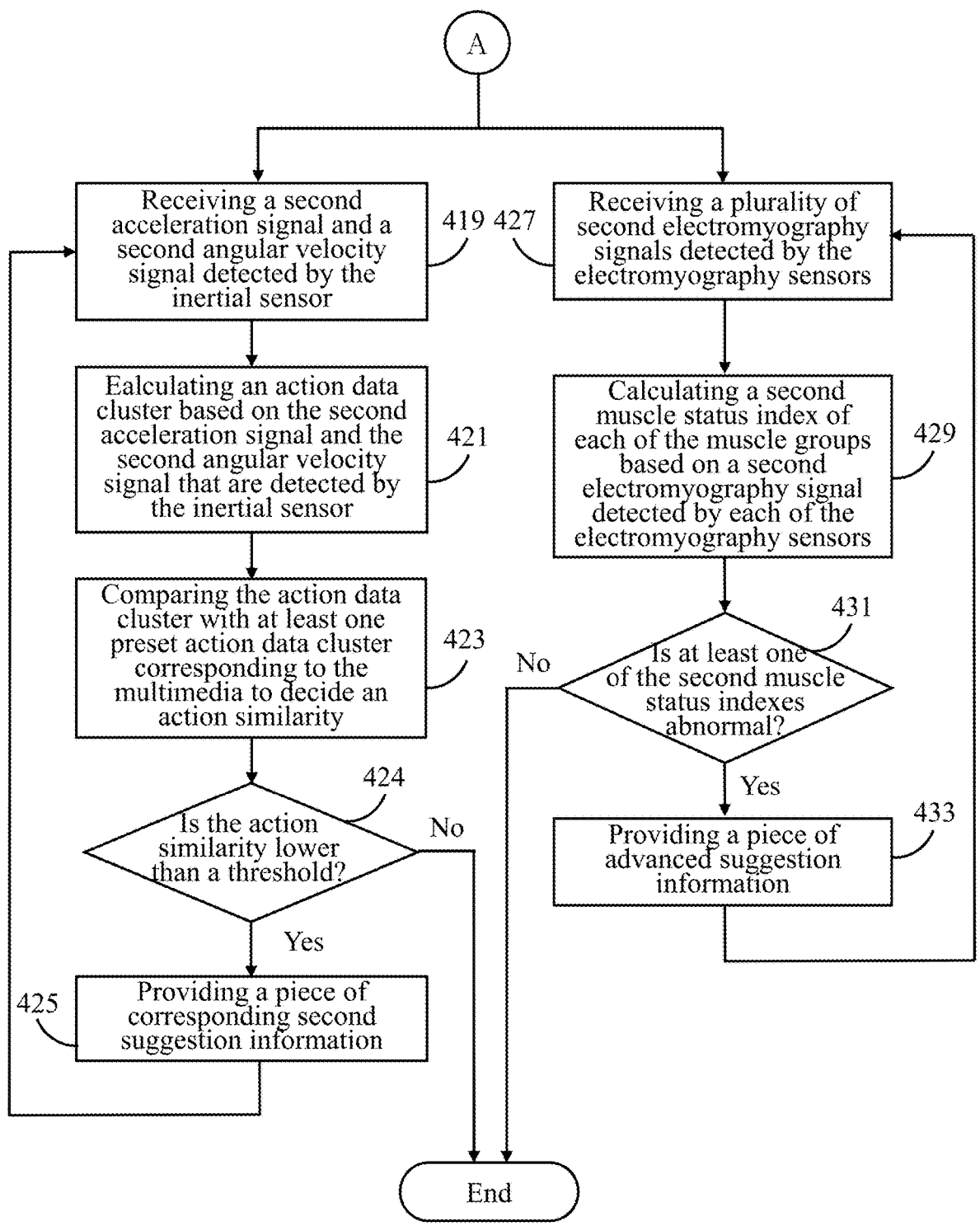
FIG. 4B is a flowchart illustrating a method for providing body posture health information in one or more embodiments of the present invention.

FIG. 4A to FIG. 4B illustrate a method for providing body posture health information in one or more embodiments of the present invention. It shall be appreciated that the method shown in FIG. 4A to FIG. 4B is only an example and is not used to limit the present invention. Referring to FIG. 4A to FIG. 4B, the method for providing body posture health information of the present invention may comprise steps 401 to 433.

In step 401, a first acceleration signal and a first angular velocity signal detected by an inertial sensor disposed on at least one part of a human body are received by a communication unit. In step 403, a posture data cluster is calculated by a processor based on the first acceleration signal and the first angular velocity signal that are detected by the inertial sensor. In step 405, the posture data cluster is compared with each of a plurality of preset posture data clusters individually by the processor to determine whether the posture data cluster matches one of the preset posture data clusters. If the determination result of the step 405 is No (i.e., the posture data cluster does not match any of the preset posture data clusters), the step 401 is executed to process the next batch of first acceleration signal and angular velocity signal. If the determination result of the step 405 is Yes (i.e., the posture data cluster matches one of the preset posture data clusters), step 407 is executed to generate a feedback message by the processor. In some embodiments, the feedback message is a correct posture prompting message when the posture data cluster matches a correct posture data cluster among the preset posture data clusters; and the feedback message is an incorrect posture prompting message when the posture data cluster matches an incorrect posture data cluster among the preset posture data clusters. In some embodiments, a feedback message may also be generated when the real-time posture data cluster does not match any of the preset posture data clusters 233 (i.e., to inform the user that the posture thereof belongs to other postures). After the step 407, the step 401 is executed to process the next batch of first acceleration signal and angular velocity signal.

In step 409, a plurality of first electromyography signals detected by a plurality of electromyography sensors disposed on a plurality of muscle groups of a human body respectively are received by the communication unit. In step 411, a first muscle status index of each of the plurality of muscle groups is calculated by the processor based on the plurality of first electromyography signals detected by the plurality of electromyography sensors. In step 413, the first muscle status indexes are compared with corresponding preset muscle status indexes individually by the processor to determine whether each of the first muscle status indexes is abnormal. If the determination result of the step 413 is that none of the first muscle status indexes is abnormal, the step 409 is executed to process the next batch of first muscle status indexes. If the determination result of the step 413 is that at least one of the first muscle status indexes is abnormal, step 415 is executed to provide a piece of first suggestion information by the processor. Thereafter, step 417 is executed to display a multimedia corresponding to the first suggestion information by a display.

In step 419, a second acceleration signal and a second angular velocity signal detected by the inertial sensor is received by the communication unit when the multimedia is displayed by the display. In step 421, an action data cluster is calculated by the processor based on the second acceleration signal and the second angular velocity signal that are detected by the inertial sensor. In step 423, the action data cluster is compared with at least one preset action data cluster corresponding to the multimedia by the processor to decide an action similarity. It shall be appreciated that, in some embodiments, each of the at least one preset action data cluster comprises a plurality of sub-action data clusters that are sequential within a time period. In step 424, it is determined whether the action similarity is lower than a threshold. If the determination result of the step 424 is No (i.e., the action similarity is not lower than the threshold), the process ends. If the determination result of the step 424 is Yes (i.e., the action similarity is lower than the threshold), step 425 is executed to provide a correspond piece of second suggestion information by the processor, and then the step 419 is executed to process the next batch of second acceleration signal and angular velocity signal.

In step 427, a plurality of second electromyography signals detected by the electromyography sensors is received by the communication unit when the multimedia is displayed by the display. In step 429, a second muscle status index of each of the muscle groups is calculated by the processor based on the second electromyography signal detected by each of the electromyography sensors. In step 431, the second muscle status indexes are compared with the corresponding preset muscle status indexes individually by the processor to determine whether each of the second muscle status indexes is abnormal. If the determination result of the step 431 is that none of the second muscle status indexes is abnormal, the process ends. If the determination result of the step 431 is that at least one of the second muscle status indexes is abnormal, step 433 is executed to provide a piece of advanced suggestion information by the processor, and then the step 427 is executed to process the next batch of second muscle status indexes.

It shall be appreciated that in FIG. 4A to FIG. 4B, the order of the steps 401 to 433 is not intended to limit the present invention, and the order may be adjusted without departing from the spirit of the present invention.

In some embodiments, the aforesaid method for providing body posture health information may be applied to the electronic apparatus 2 and/or the cloud service system 3. In other words, the electronic apparatus 2 and/or the cloud service system 3 may execute all steps shown in FIG. 4A to FIG. 4B. How the method for providing body posture health information accomplishes corresponding steps of the operations shall be directly appreciated by those of ordinary skill in the art based on the above descriptions of the electronic apparatus 2 and/or the cloud service system 3, and thus will not be further described herein.

The above invention is related to the detailed technical contents and inventive features thereof. People skilled in this field may proceed with a variety of modifications and replacements based on the inventions and suggestions of the invention as described without departing from the characteristics thereof. Nevertheless, although such modifications and replacements are not fully disclosed in the above descriptions, they have substantially been covered in the following claims as appended.

What is claimed is:

1. An electronic apparatus for providing body posture health information, comprising:
   a processor;
   a storage apparatus electrically connected to the processor, being configured to store a computer program, a plurality of preset posture data clusters, a plurality of preset muscle status indexes, and a plurality of preset action data clusters, wherein each of the preset muscle status indexes corresponds to one of a plurality of muscle groups; and
   a display,
   wherein the processor executes a posture calculation program of the computer program to calculate a posture data cluster based on a first acceleration signal and a first angular velocity signal that are detected by an inertial sensor disposed at least partially on at least one part of a human body,
   wherein the processor executes a posture comparison program of the computer program to determine that the posture data cluster matches one of the preset posture data clusters by comparing the posture data cluster with each of the plurality of preset posture data clusters individually,
   wherein the processor executes a posture feedback program of the computer program to generate a feedback message in response to the determination that the posture data cluster matches one of the preset posture data clusters,
   wherein the processor executes a muscle status calculation program of the computer program to calculate a first muscle status index of each of a plurality of muscle groups on the human body based on a plurality of first electromyography signals detected by a plurality of electromyography sensors disposed on the plurality of muscle groups of the human body, and each of the first muscle status indexes corresponds to one of the muscle groups,
   wherein the processor executes a muscle status comparison program of the computer program to determine that one of the first muscle status indexes is abnormal by comparing each of the first muscle status indexes with the preset muscle status index that corresponds to the same muscle group,
   wherein the processor executes a muscle status feedback program of the computer program to provide a piece of first suggestion information, wherein the first suggestion information corresponds to a multimedia, and the multimedia corresponds to at least one of the preset action data clusters, wherein the display is, configured to display the multimedia, wherein the processor executes an action calculation program of the computer program to calculate an action data cluster based on a second acceleration signal and a second angular velocity signal that is detected by the inertial sensor, wherein the processor executes an action comparison program of the computer program to compare the action data cluster with the at least one preset action data cluster corresponding to the multimedia to decide an action similarity, wherein the action similarity is lower than a threshold, and wherein the processor executes an action feedback program of the computer program to provide a piece of second suggestion information.

2. The electronic apparatus of claim 1, wherein the posture data cluster matches a correct posture data clusters among the preset posture data clusters, and the feedback message is a correct posture prompting message.

3. The electronic apparatus of claim 1, wherein the posture data cluster matches an incorrect posture data cluster among the preset posture data clusters, and the feedback message is an incorrect posture prompting message.

4. The electronic apparatus of claim 1, wherein each of the preset action data clusters comprises a plurality of sub-action data clusters that are sequential within a time period.

5. The electronic apparatus of claim 1, wherein the muscle status calculation program calculates a second muscle status index of each of the muscle groups based on a second electromyography signal detected by each of the electromyography sensors after the multimedia is displayed by the display, the muscle status comparison program compares the second muscle status indexes with the corresponding preset muscle status indexes individually to determine whether each of the second muscle status indexes is abnormal, and the muscle status feedback program provides a piece of advanced suggestion information when at least one of the second muscle status indexes is abnormal.

6. The electronic apparatus of claim 1, further comprising: a communication unit electrically connected to the processor, being configured to receive the first acceleration signal and the first angular velocity signal from the inertial sensor via a near-end network and receive the first electromyography signals detected by the electromyography sensors via the near-end network.

7. A system for providing body posture health information, comprising:

a processor;

a communication apparatus electrically connected to the processor and communicating with an electronic apparatus via a remote network; and a storage apparatus electrically connected to the processor, being configured to store a computer program, a plurality of preset posture data clusters, a plurality of preset muscle status indexes, and a plurality of preset action data clusters, wherein each of the preset muscle statuses index corresponds to one of a plurality of muscle groups, wherein the processor executes a posture calculation program of the computer program to calculate a posture data cluster based on a first acceleration signal and a first angular velocity signal that is detected by an inertial sensor disposed at least partially on at least one part of a human body, wherein the processor executes a posture comparison program of the computer program to determine that the posture data cluster matches one of the preset posture data clusters by comparing the posture data cluster with each of the plurality of preset posture data clusters individually, wherein the processor executes a posture feedback program of the computer program to generate a feedback message in response to the determination that the posture data cluster matches one of the preset posture data clusters, wherein the processor executes a muscle status calculation program of the computer program to calculate a first muscle status index of each of the plurality of muscle groups on the human body based on a plurality of first electromyography signals detected by a plurality of electromyography sensors disposed on the plurality of muscle groups of the human body, and each of the first muscle status indexes corresponds to one of the muscle groups, wherein the processor executes a muscle status comparison program of the computer program to determine that one of the first muscle status indexes is abnormal by comparing each of the first muscle status indexes with the preset muscle status index that corresponds to the same muscle group, wherein the processor executes a muscle status feedback program of the computer program to provide a piece of first suggestion information, wherein the communication apparatus transmits the first suggestion information to the electronic apparatus via the remote network so that a display of the electronic apparatus displays a multimedia corresponding to the first suggestion information, and the multimedia corresponds to at least one of the preset action data clusters, wherein the processor executes an action calculation program of the computer program to calculate an action data cluster based on a second acceleration signal and a second angular velocity signal that is detected by the inertial sensor, wherein the processor executes an action comparison program of the computer program to compare the action data cluster with the at least one preset action data cluster corresponding to the multimedia to decide an action similarity, wherein the action similarity is lower than a threshold, and wherein the processor executes an action feedback program of the computer program to provide a piece of second suggestion information.

8. The system of claim 7, wherein the posture data cluster matches a correct posture data cluster among the preset posture data clusters, and the feedback message is a correct posture prompting message.

9. The system of claim 7, wherein the posture data cluster matches an incorrect posture data cluster among the preset posture data clusters, and the feedback message is an incorrect posture prompting message.

10. The system of claim 7, wherein each of the preset action data clusters comprises a plurality of sub-action data clusters that are sequential within a time period.

11. The system of claim 7, wherein the muscle status calculation program calculates a second muscle status index of each of the muscle groups based on a second electromyography signal detected by each of the electromyography sensors after the multimedia is displayed by the display, the muscle status comparison program compares the second muscle status indexes with the corresponding preset muscle status indexes individually to determine whether each of the second muscle status indexes is abnormal, and the muscle status feedback program provides a piece of advanced suggestion information when at least one of the second muscle status indexes is abnormal.

12. The system of claim 7, wherein the communication apparatus further receives the first acceleration signal and the first angular velocity signal from the inertial sensor via the electronic apparatus and receive the first electromyography signals detected by the electromyography sensors via the electronic apparatus.

13. A method for providing body posture health information, comprising:
   calculating, by a processor, a posture data cluster based on a first acceleration signal and a first angular velocity signal that is detected by an inertial sensor disposed at least partially on at least one part of a human body;
   determining, by the processor, that the posture data cluster matches one of a plurality of preset posture data clusters by comparing the posture data cluster with each of the preset posture data clusters individually;
   generating, by the processor, a feedback message in response to the determination that the posture data cluster matches one of the preset posture data clusters;
   calculating, by the processor, a first muscle status index of each of a plurality of muscle groups on the human body based on a plurality of first electromyography signals detected by a plurality of electromyography sensors disposed on the plurality of muscle groups of the human body, wherein each of the first muscle status indexes corresponds to one of the muscle groups, and each of a plurality of preset muscle status indexes corresponds to one of the muscle groups ;
   determining, by the processor, that one of the first muscle status indexes is abnormal by comparing each of the first muscle status indexes with the preset muscle status index that corresponds to the same muscle group;
   providing, by the processor, a piece of first suggestion information;
   displaying, by a display, a multimedia corresponding to the first suggestion information, and the multimedia corresponds to at least one of the preset action data clusters;
   calculating, by the processor, an action data cluster based on a second acceleration signal and a second angular velocity signal that is detected by the inertial sensor;
   comparing, by the processor, the action data cluster with the at least one preset action data cluster corresponding to the multimedia to decide an action similarity, wherein the action similarity is lower than a threshold; and
   providing, by the processor, a piece of second suggestion information.

14. The method of claim 13, wherein the posture data cluster matches a correct posture data cluster& among the preset posture data clusters, and the feedback message is a correct posture prompting message.

15. The method of claim 13, wherein the posture data cluster matches an incorrect posture data cluster among the preset posture data clusters, and the feedback message is an incorrect posture prompting message.

16. The method of Claim 13, wherein each of the at least one preset action data cluster comprises a plurality of sub-action data clusters that are sequential within a time period.

17. The method of claim 13, further comprising the following steps:
   calculating, by the processor, a second muscle status index of each of the muscle groups based on a second electromyography signal detected by each of the electromyography sensors after the multimedia is displayed by the display;
   comparing, by the processor, the second muscle status indexes with the corresponding preset muscle status indexes individually to determine whether each of the second muscle status indexes is abnormal; and
   providing, by the processor, a piece of advanced suggestion information when at least one of the second muscle status indexes is abnormal.

18. The method of claim 13, further comprising the following steps:
   receiving, by a communication unit, the first acceleration signal and the first angular velocity signal from the inertial sensor; and
   receiving, by a communication unit, the first electromyography signals detected by the electromyography sensors.

* * * * *